US006527979B2

(12) United States Patent
Constantz et al.

(10) Patent No.: US 6,527,979 B2
(45) Date of Patent: *Mar. 4, 2003

(54) CATHETER SYSTEMS AND METHODS FOR THEIR USE IN THE TREATMENT OF CALCIFIED VASCULAR OCCLUSIONS

(75) Inventors: Brent R. Constantz, Menlo Park, CA (US); Peter K. Johansson, Campbell, CA (US); Erin McGurk, Palo Alto, CA (US)

(73) Assignee: Corazon Technologies, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/384,860

(22) Filed: Aug. 27, 1999

(65) Prior Publication Data

US 2002/0044907 A1 Apr. 18, 2002

(51) Int. Cl.[7] ............................................... A61B 17/06
(52) U.S. Cl. ...................... 252/364; 604/523; 424/666; 424/680; 206/438; 423/481
(58) Field of Search ................... 604/500, 523, 604/96.01, 508; 423/481; 424/666, 663, 680; 436/18; 252/364; 206/438

(56) References Cited

U.S. PATENT DOCUMENTS

| | | | |
|---|---|---|---|
| 3,859,228 A | * | 1/1975 | Morishita et al. ............ 252/364 |
| 3,892,818 A | * | 7/1975 | Scharfe et al. ........... 260/676 R |
| 4,065,366 A | * | 12/1977 | Oda et al. .................... 204/296 |
| 4,202,760 A | * | 5/1980 | Storey et al. ............ 137/101.11 |
| 4,208,404 A | * | 6/1980 | Cowan ........................ 424/677 |
| 4,329,994 A | | 5/1982 | Cooper |
| 4,336,881 A | * | 6/1982 | Babb et al. .................. 206/525 |
| 4,445,892 A | | 5/1984 | Hussein et al. |
| 4,573,966 A | | 3/1986 | Weikl et al. |
| 4,610,662 A | | 9/1986 | Weikl et al. |
| 4,636,195 A | | 1/1987 | Wolinsky |
| 4,655,746 A | | 4/1987 | Daniels et al. |
| 4,690,672 A | | 9/1987 | Veltrup |

(List continued on next page.)

OTHER PUBLICATIONS

Hargrove III et al. (Dec. 1982), "Treatment of Acute Peripheral Arterial and Graft Thromboses with Low–Dose Streptokinase," *Surgery*, vol. 92(6):981–993.
Koltun et al. (Aug. 1987), "Thrombolysis in the Treatment of Peripheral Arterial Vascular Occlusions," *Arch Surg*, vol. 122:901–905.
Olin et al. (Nov. 1988), "Thrombolytic Therapy in the Treatment of Peripheral Arterial Occlusions," *Annals of Emergency Medicine*, vol. 17:1210/125–1215/130.
Rickard et al. (Dec. 1997), "Limitations of Intra–Arterial Thrombolysis," *Cardiovascular Surgery*, vol. 5(6):634–640.

*Primary Examiner*—Brian L. Casler
*Assistant Examiner*—Jeremy Thissell
(74) *Attorney, Agent, or Firm*—Bret E. Field; Bozicevic, Field & Francis

(57) ABSTRACT

Catheter systems and methods for their use in enhancing fluid flow through a vascular site occupied by a vascular occlusion are provided. The subject catheter systems include at least an aspiration catheter and at least one of a total occlusion insert catheter and a partial occlusion insert catheter, where the insert catheters are capable of being slidably moved in the lumen of the aspiration catheter. In practicing the subject methods, a surface of the vascular occlusion is flushed with an acidic dissolution fluid using the subject catheter systems for a period of time sufficient for fluid flow through the vascular site to be enhanced, e.g. increased or established. The subject catheter systems and methods find use in the treatment of a variety of different vascular diseases characterized by the presence of calcified vascular occlusions, including peripheral and coronary vascular diseases.

18 Claims, 14 Drawing Sheets

U.S. PATENT DOCUMENTS

| | | |
|---|---|---|
| 4,824,436 A | 4/1989 | Wolinsky |
| 4,838,881 A | 6/1989 | Bennett |
| 4,911,163 A | 3/1990 | Fina |
| 4,976,733 A | 12/1990 | Girardot |
| 5,059,178 A | 10/1991 | Ya |
| 5,090,960 A | 2/1992 | Don Michael |
| 5,149,330 A | 9/1992 | Brightbill |
| 5,167,623 A | 12/1992 | Cianci et al. |
| 5,167,628 A | 12/1992 | Boyles |
| 5,195,955 A | 3/1993 | Don Michael |
| 5,207,648 A | 5/1993 | Gross |
| 5,222,941 A | 6/1993 | Don Michael |
| 5,370,609 A | 12/1994 | Drasler et al. |
| 5,380,284 A | 1/1995 | Don Michael |
| 5,443,446 A | 8/1995 | Shturman |
| 5,462,529 A | 10/1995 | Simpson et al. |
| 5,496,267 A | 3/1996 | Drasler et al. |
| 5,542,937 A | 8/1996 | Chee et al. |
| 5,594,125 A * | 1/1997 | Seyschab et al. ........ 106/162.1 |
| 5,785,675 A | 7/1998 | Drasler et al. |
| 5,833,650 A | 11/1998 | Imran |
| 5,942,410 A * | 8/1999 | Lam et al. ................. 435/40.5 |
| 6,013,068 A | 1/2000 | Spiegelhalter |
| 6,123,966 A * | 9/2000 | Kross ......................... 210/764 |
| 6,156,350 A * | 12/2000 | Constantz ................... 424/666 |
| 6,242,388 B1 * | 6/2001 | Sharma et al ................. 134/40 |

* cited by examiner

CATHETER SYSTEMS AND METHODS FOR THEIR USE IN THE TREATMENT OF CALCIFIED VASCULAR OCCLUSIONS

TECHNICAL FIELD

The field of this invention is vascular disease, particularly vascular diseases characterized by the presence of calcified vascular occlusions.

BACKGROUND OF THE INVENTION

Vascular occlusions, which may be partial or total occlusions, play a prominent role in many types of vascular disease. Many vascular occlusions encountered in the treatment of vascular disease are characterized by having a mineral component, i.e. they are calcified. Calcified vascular occlusions, both partial and total, are found in both peripheral and coronary vascular disease.

A variety of different protocols have been developed for treating vascular diseases characterized by the presence of partial or total occlusions. Such treatment methodologies generally involve mechanical removal or reduction of the size of the occlusion, and include: bypass surgery, balloon angioplasty, mechanical debridement, atherectomy, and the like.

Despite the plethora of different treatment strategies that have been developed for the treatment of vascular diseases associated with vascular occlusions, there are disadvantages associated with each technique, such as tissue damage, invasiveness, etc. For example, restenosis is a common complication that results in arteries in which occlusions have been mechanically removed.

Calcified vascular occlusions pose significant challenges to currently employed treatment methodologies. For example, where the target vascular occlusion is a total occlusion, it is difficult if not impossible to pass a guidewire through the occlusion, which step is required for many of the currently used procedures. While bypass grafts are sometimes available as alternatives in such instances, bypass procedures have their own risks and complications. Furthermore, if there is no appropriate anastomosis site available, amputation is often the only alternative.

As such, there is continued interest in the development endovascular methods of treating vascular occlusions. Of particular interest would be the development of methods and devices suitable for use in the treatment of calcified vascular occlusions.

Relevant Literature

U.S. Patents of interest include: U.S. Pat. Nos. 4,445,892; 4,573,966; 4,610,662; 4,636,195; 4,655,746; 4,690,672; 4,824,436; 4,911,163; 4,976,733; 5,059,178; 5,090,960; 5,167,628; 5,195,955; 5,222,941; 5,370,609; 5,380,284; 5,443,446; 5,462,529; 5,496,267 and 5,785,675. See also: Koltun et al., Arch. Surg. (August 1987) 122:901–905; Olin et al., Ann. Emerg. Med. (November 1988) 17:1210–1215; Hargrove et al., Surgery (December 1982) 92:981–993; and Rickard et al., Cardiovascular Surg. (December 1997) 5:634–640. See also Peripheral Endovascular Interventions, $2^{nd}$ ed. (White & Fogarty eds., Springer, N.Y.)(1996) pp 565–576.

SUMMARY OF THE INVENTION

Catheter systems and methods are provided for enhancing fluid flow, i.e. blood flow, through a vascular site occupied by a vascular occlusion. The subject catheter systems include at least an aspiration catheter and at least one of a total occlusion insert catheter and a partial occlusion insert catheter, where the insert catheters are capable of being slidably moved within the aspiration lumen of the aspiration catheter. In practicing the subject methods, a surface of the vascular occlusion is flushed with an acidic dissolution fluid using the subject catheter systems for a period of time sufficient for fluid flow through the vascular site to be enhanced, e.g. increased or established. The subject catheter systems and methods find use in the treatment of a variety of different vascular diseases characterized by the presence of calcified vascular occlusions, including peripheral and coronary vascular diseases.

DESCRIPTION OF THE SPECIFIC EMBODIMENTS

Figure 1A:
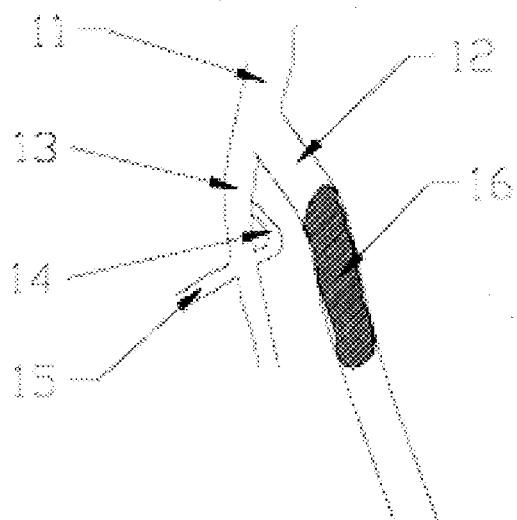
FIGS. 1A and 1B provide a representation of a totally occluded superficial femoral artery and a partially occluded superficial femoral artery, respectively.

Catheter systems and methods for their use to enhance fluid flow through a vascular site occupied by a vascular occlusion are provided. The subject catheter systems include at least an aspiration catheter and at least one of a total occlusion or partial occlusion catheter insert. In practicing the subject methods, the catheter systems are used to contact a surface of the target vascular occlusion for a period of time sufficient to enhance, e.g. establish or improve, fluid flow through the vascular site occupied by the target occlusion. The subject systems and methods find use in the treatment of a variety of vascular disease conditions characterized by the presence of vascular occlusions, including peripheral and coronary vascular disease conditions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Catheter Systems

As summarized above, the subject invention provides catheter systems suitable for delivery of a fluid to a vascular site, and particularly for delivery of an acidic dissolution fluid to a surface of vascular occlusion. By catheter system is meant two more disparate catheter components which are capable of being assembled into a single unit, i.e. coaxial catheter assembly, having an inner catheter that is slidably positioned within the lumen of an outer catheter, i.e. a coaxial catheter assembly having an inner insert catheter that can be moved relative to the outer catheter so as to produce varying distances between the distal ends of the two coaxial catheters.

Aspiration Catheter

The aspiration catheter is generally an elongated tubular structure fabricated from a flexible, biologically acceptable material having a balloon or analogous vessel occlusion means positioned at its distal end. The length of the aspiration catheter may vary, but is generally from about 80 to 200 cm, usually from about 90 to 180 cm and more usually from about 100 to 140 cm. The outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). The aspiration catheter is characterized by having an open distal end, where the inner diameter at the open distal end is sufficient to house either a partial or total occlusion insert catheter and remove fluid from the vascular site at the desired rate, e.g. a rate that provides for substantially isometric or isobaric pressure in the vascular site during treatment, through the resultant annular space. The aspiration catheter at least includes an aspiration lumen. The inner diameter of the aspiration lumen, at least at its distal end and generally along the entire length of the aspiration catheter, typically ranges from about 0.2 to 2.0, usually from about 0.25 to 1.75 and more usually from about 0.35 to 1.5 mm. Also present at the distal end of the aspiration catheter is a vessel occlusion means, where the vessel occlusion means is usually an inflatable balloon. The balloon is one that is inflatable to a volume sufficient to substantially occlude the vessel in which the aspiration catheter is positions, e.g. by against the intimal surface of the vessel in which the aspiration catheter is positioned. The balloon is in fluid or gaseous communication with an inflation lumen that runs the length of the aspiration catheter and can be connected to a balloon inflation means. The inflation lumen has an inner diameter that typically ranges from about 0.1 to 0.5, usually from about 0.2 to 0.4 mm. In certain embodiments, the aspiration catheter further includes a separate guidewire lumen. When present, the guidewire lumen has a diameter ranging from about 0.2 to 1.0 mm, usually from about 0.3 to 0.6 mm. Thus, the aspiration catheter includes at least two distinct lumens, i.e. an aspiration lumen and a balloon inflation lumen, and in many embodiments includes three distinct lumens, i.e. an aspiration lumen, a balloon inflation lumen and a guidewire lumen.

Figure 2A:
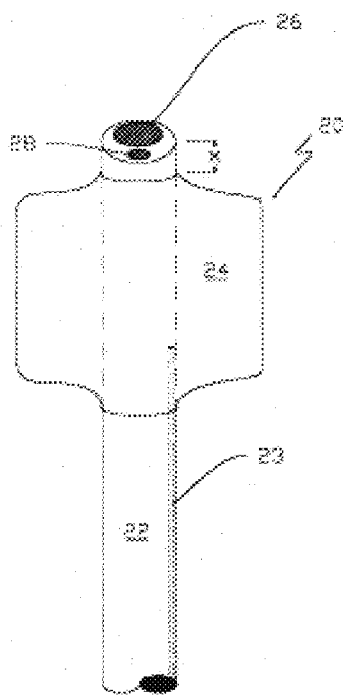
FIGS. 2A and 2B provide representations of the aspiration catheter and the total occlusion insert catheter, respectovely, while FIG. 2C provides a representation of the total occlusion insert catheter inserted into the lumen of the aspiration catheter to form a coaxial catheter assembly for use in the methods of the subject invention.

A representation of the aspiration catheter of the subject catheter systems found in the subject kits is provided in FIG. 2A. In FIG. 2A, aspiration catheter 20 includes elongated tubular member 22 and balloon 24 located proximal to the distal end. The distance X between the distal most portion of the balloon 24 and the distal end of the catheter typically ranges from about 1 to 20, usually from about 5 to 10 mm. Also shown is distal open end 26 through which either the partial or total occlusion insert catheter is moved and fluid is aspirated. Balloon 24 is inflatable via balloon inflation lumen 23. Finally, device 20 is shown with optional guidewire lumen 28.

The aspiration catheter is further characterized by being capable of attaching, either directly or through one or more attachment means, at its proximal end to vacuum means, e.g. a negative pressure means, where such means is sufficient to provide for the desired aspiration during use of the device, and a balloon inflation means, where such means is sufficient to inflate the balloon at the distal end of the catheter when desired.

Catheter Inserts

As mentioned above, the subject catheter systems also include at least one catheter insert, where the catheter insert is capable of being slidably positioned within the lumen of the aspiration catheter and is either a total occlusion catheter insert or a partial occlusion catheter insert.

Figure 2B:
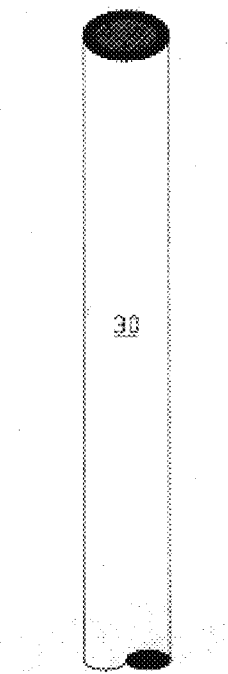

The total occlusion catheter insert is an elongated tubular structure having a blunt ended, open distal end through which fluid may be flowed under pressure. The length of the total occlusion catheter insert generally ranges from about 90 to 210 cm, usually from about 100 to 190 cm and more usually from about 110 to 150 cm. The outer diameter of the total occlusion catheter insert is such that the catheter insert may be slidably positioned in the lumen of the aspiration catheter, and typically ranges from about 0.5 to 2.0, usually from about 0.8 to 1.6 mm. The inner diameter of the total occlusion catheter insert typically ranges from about 0.2 to 1.0, usually from about 0.25 to 1.0 and more usually from about 0.3 to 1.0 mm. The total occlusion catheter insert (as well as the other catheter components of the subject catheter systems) generally has a circular cross-sectional shape, but the cross-sectional shape could be any convenient cross-sectional shape, including ovoid, irregular etc. A representation of a total occlusion catheter insert 30 according to the subject invention is provided in FIG. 2B.

Figure 2C:
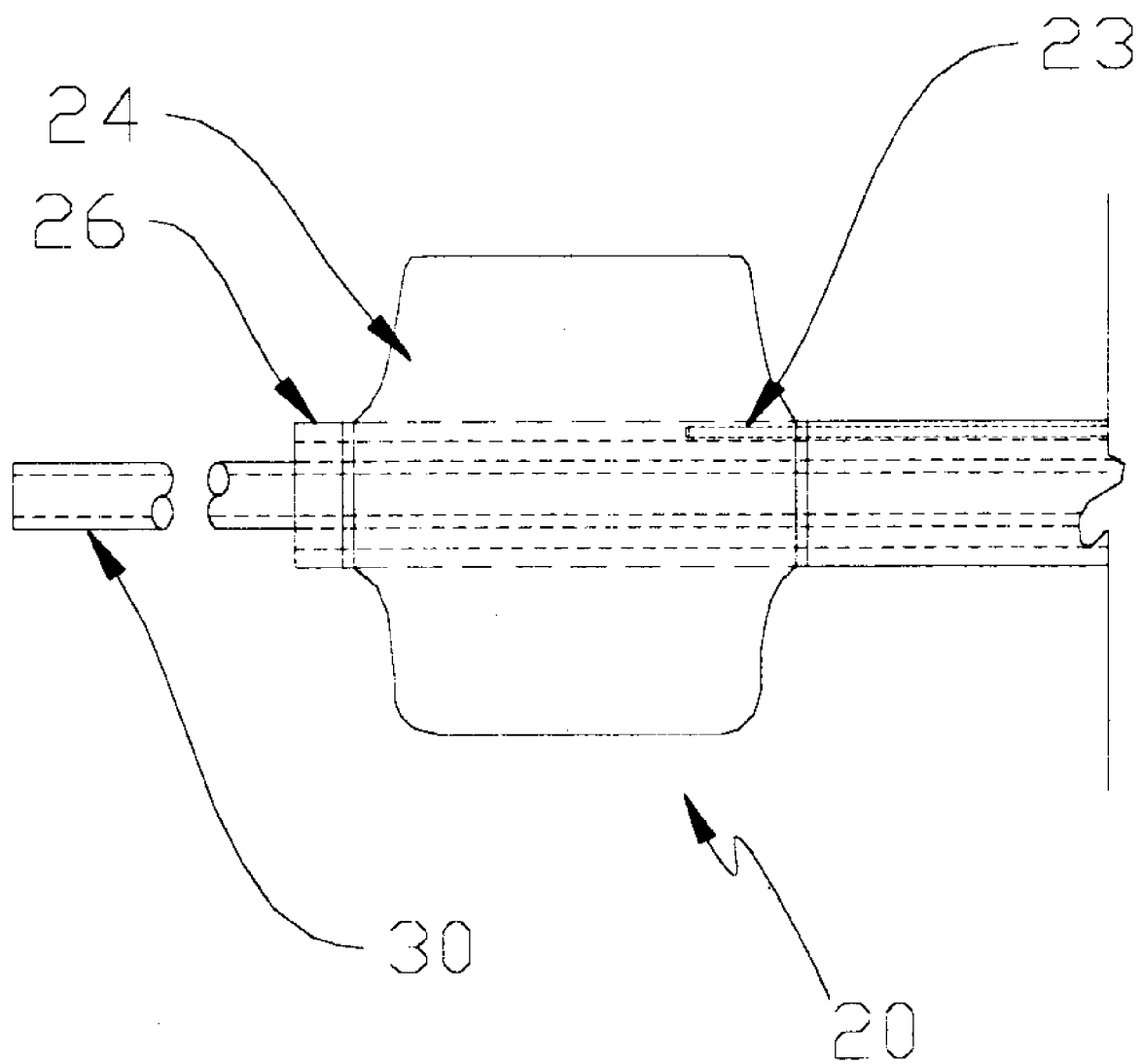

A representation of the total occlusion catheter insert positioned inside the lumen of an aspiration catheter (i.e. as a coaxial catheter assembly) and ready for use in the subject methods, as described infra, is provided in FIG. 2C. In the coaxial catheter assembly shown in FIG. 2C, the total occlusion catheter insert and the aspiration catheter are coaxial catheters. In FIG. 2C, total occlusion catheter insert 30 is slidably positioned in the lumen of aspiration catheter 20. Also shown is occlusion balloon 24 which is inflated and deflated through fluid/gaseous flow through balloon inflation lumen 23.

Alternatively or in addition to the total occlusion catheter insert described above, the subject catheter systems may also include a partial occlusion catheter insert. The partial occlusion catheter insert differs from the total occlusion catheter insert in a number of ways. First, the total occlusion vascular insert includes a balloon or analogous vessel occlusion means at its distal end. Second, the total occlusion vascular insert has one or more fluid introduction ports proximal to the proximal side of the distal balloon. Finally, the end of the partial occlusion catheter insert is sealed. The length of the partial occlusion catheter insert generally ranges from about 90 to 250 cm, usually from about 100 to 230 cm and more usually from about 110 to 190 cm. The outer diameter of the partial occlusion catheter insert is such that the catheter insert may be slidably positioned in the aspiration lumen of the aspiration catheter, and typically ranges from about 0.5 to 2.0, usually from about 0.8 to 1.6 mm. The inner diameter of the total occlusion catheter insert typically ranges from about 0.2 to 1.0, usually from about 0.25 to 1.0 and more usually from about 0.3 to 1.0 mm.

Figure 3A:
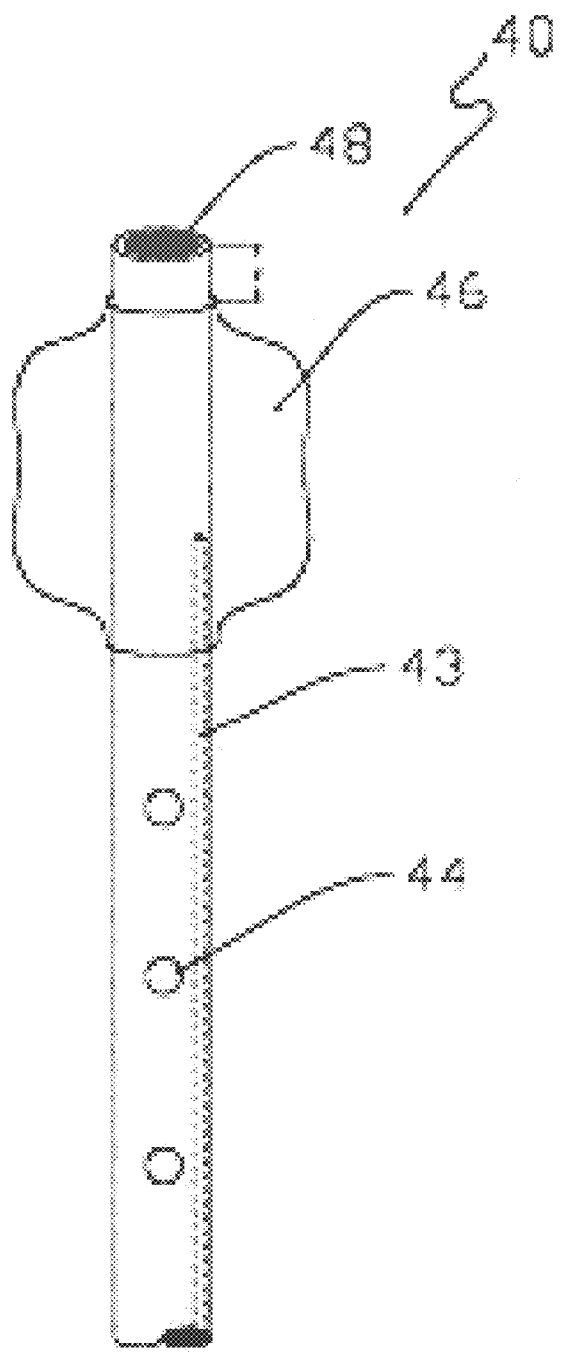
FIG. 3A provides a representation of a partial occlusion insert catheter while FIG. 3B provides a representation of the partial occlusion insert catheter inserted into the lumen of the aspiration catheter of FIG. 2A to form a coaxial catheter assembly for use in the methods of the subject invention.

A representative partial occlusion catheter insert is provided in FIG. 3A. In FIG. 3A, partial occlusion catheter insert 40 includes elongated tubular structure 42 that is sealed at its distal end 48. Proximal to the distal end 48 is balloon 46, where the distance Y typically ranges from about 1 to 30 mm, usually from about 10 to 20 mm. Also depicted are infusion ports 44. The diameter of the infusion ports may vary, but typically ranges from about 0.2 to 1.2, usually from about 0.4 to 1.0 and more usually from about 0.5 to 0.8 mm. Also shown is balloon inflation lumen 43, where the balloon inflation lumen has dimensions similar to those of balloon inflation lumen 23. As evidenced, the partial occlusion catheter insert includes two lumens, a fluid introduction lumen and a balloon inflation lumen.

Figure 3B:
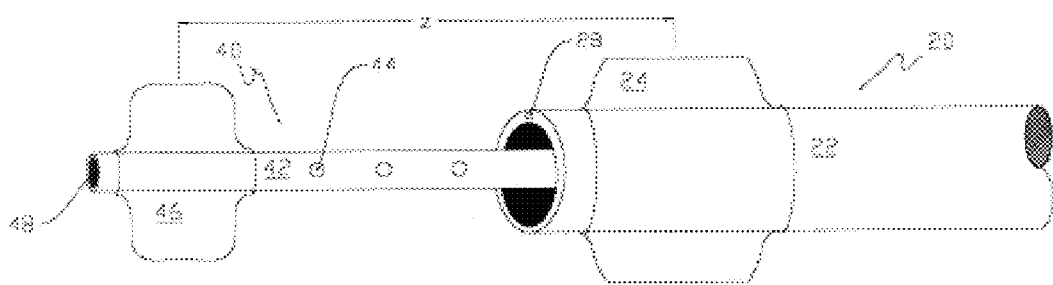

FIG. 3B shows the catheter assembly produced by insertion of the partial occlusion catheter into the aspiration catheter. In FIG. 3B, partial occlusion catheter 40 is slidably positioned in the lumen of aspiration catheter 20. As the two catheters are slidably positioned with respect to one another, the distance Z between the two balloons may vary, where during any given treatment procedure the distance Z may range from 1.5 to 45, usually from about 2 to 30 cm. Infusion ports 44 provided for entry of a solution into the occluded space and fluid is then aspirated through the distal end of the aspiration catheter.

The catheter inserts are further characterized by being capable of being attached at their proximal ends, either directly or through one or more attachment means, to a fluid reservoir, e.g. an acidic dissolution fluid reservoir and, in the case of the partial occlusion catheter insert, a balloon inflation means.

Further Catheter System Characteristics

The components of the subject catheter systems, as described above, may be fabricated from any convenient material, with the only limitation being that at least the catheter inserts and the aspiration catheter be fabricated from a material that withstands, i.e. does not degrade upon contact with, the acidic dissolution fluid, at least for the period of time during which the catheter system is used. The materials must also be able to withstand the effects of any reaction byproducts produced by contact of the acidic dissolution solution with the components of the target occlusion. Suitable materials include biocompatible polymers, e.g. polyimide, PBAX™, polyethylene, and the like. Any glues or fittings that are employed must also be able to meet the same criteria. Any convenient fabrication protocol may be employed, where numerous suitable protocols are known to those of skill in the art.

While the above described catheter systems have been described in terms of an outer aspiration catheter and a catheter insert which serves to introduce fluid into a vascular site, i.e. as a fluid introduction means, during use of the subject systems (as described in greater detail below) these relative functions may be reversed, such that fluid is introduced through the outer, aspiration catheter and removed through the catheter insert.

Methods

Also provided by the subject invention are methods of locally introducing active agents to vascular sites. In the broadest sense, the subject catheter systems may be employed to introduce any active agent in a fluid delivery vehicle to a vascular site. The subject systems achieve local delivery of active agents in fluid delivery vehicles by irrigating or flushing a portion of the vascular system with the fluid agent composition. Active agents of interest that may be locally introduced using the subject methods include: thrombolyhtic agents, growth factors, cytokines, nucleic acids (e.g. gene therapy agents), detergents and surfactants, and the like. Of particular interest is the use of the subject catheter systems in the treatment of vascular calcified occlusions, which application will now be described in greater detail as representative of the various methods in which the subject catheter systems may be introduced.

For treatment of vascular calcified occlusions with the subject catheter systems, the subject catheter systems are used to flush a surface of the target vascular occlusion with an acidic dissolution fluid for a period of time sufficient for fluid flow to be to be enhanced through the vascular site. As indicated above, by enhanced is meant that fluid flow is either established in situations where fluid flow is not initially present, e.g. where the target vascular occlusion is a total occlusion, or increased where some fluid flow through the vascular site is present, e.g. in situations where the vascular site is occupied by a partial occlusion.

The Target Vascular Site

The target site through which fluid flow is enhanced by the subject methods is a site within a vessel, typically an artery or vein, and usually an artery. In many embodiments, the vascular site is a peripheral vascular site, by which is meant that the vessel in which the vascular site is located is a vessel found in one of the extremities of the patient to be treated, i.e. the arms or legs. Often, the vascular site is a site in a lower extremity vessel, e.g. a lower extremity artery. As indicated above, of particular interest are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g. the aorta, a coronary artery or branch vessel thereof, etc. In yet other embodiments, the vascular site is present in a carotid artery or a branch vessel thereof.

The vascular site is occupied by a vascular occlusion in such a manner that fluid flow through the vascular site, e.g. blood flow, is at least impeded if not substantially inhibited. By at least impeded is meant that fluid flow is reduced by at least 20%, usually by at least 50% and more usually by at least 80% through the vascular site as compared to a control. In such situations, the vascular site is occupied by a partial vascular calcified occlusion. By substantially inhibited is meant that substantially no fluid flows through the vascular site. For purposes of this invention, fluid flow through a vascular site is considered to be substantially inhibited where it is not possible to pass a guidewire through the vascular site, where the guidewire has a diameter ranging from 0.014 to 0.038 in and is applied to the site with a pressure ranging from about 1 to 30 oz.

Figure 1B:
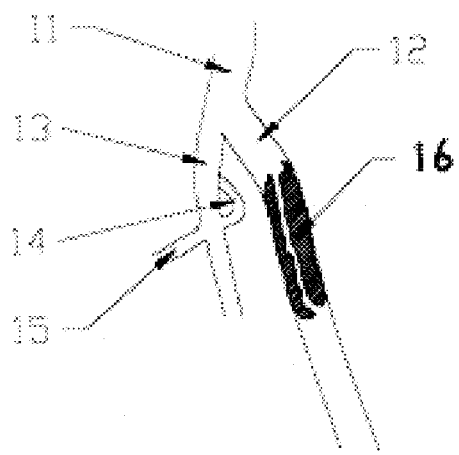

A representation of a peripheral artery having a vascular site occupied by a total vascular calcified occlusion is provided in FIG. 1A while a representation of a peripheral artery having a vascular site occupied by a partial vascular calcified occlusion is provided in FIG. 1B.

The Target Vascular Occlusion

The vascular occlusion that occupies the target vascular site is generally a calcified vascular occlusion, by which is meant that the occlusion includes at least some calcium containing component. The calcified occlusion may be a substantially pure mineral structure, or may be a more complex formation that includes both mineral and other components, including organic matter, e.g. lipids, proteins, and the like. As mentioned above, the target vascular occlusion may be a partial or total vascular occlusion.

The mineral component making up the calcified lesion is generally made up of one or more calcium phosphates, where the calcium phosphates are generally apatitic. The term "apatite" as used herein refers to a group of phosphate minerals that includes ten mineral species and has the general formula $X_5(YO_4)_3Z$, where X is usually $Ca^{2+}$ or $Pb^{3-}$, Y is $P^{5+}$ or $As^{5+}$, an is $F^-$, $Cl^-$, or $OH^-$. The term calcium apatite refers to a group of phosphate minerals where X is $Ca^{2+}$. The mineral component of the calcified occlusion typically includes one or more of hydroxyapatite, carbonated hydroxyapatite (dahllite) and calcium deficient hydroxyapatite.

In addition to the mineral component, the calcified occlusion that occupies the target vascular site may also comprise one or more additional components, where such components include: lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. As such, calcified occlusions that are targets of the subject methods include those that may be described as: type IV, type V and type VI lesions, as defined in Stary et al., Arterioscler. Thromb. Vasc. Biol. (1995) 15:1512–1531.

In the vascular occlusions that occupy the target vascular sites of the subject methods, the mineral component of the calcified occlusion generally makes up from about 10 to 100, usually from about 10 to 90 and more usually from about 10 to 85 dry weight % of the occlusion. The size of the occlusion that is the target of the subject methods varies depending on location and specific nature of the occlusion. Generally, the volume of the occlusion will range from about 20 to 10,000 $mm^3$, usually from about 30 to 500 $mm^3$ and more usually from about 50 to 300 $mm^3$.

In certain embodiments, one or both ends of the occlusion may be characterized by being primarily thrombotic material, e.g. a thrombus, where the thrombotic domain of the occlusion extends for about 1 to 5 cm. The nature of the thrombotic domain may be organized or disorganized.

Contacting the Vascular Occlusion with an Acidic Dissolution Fluid

In the subject methods, one surface of the vascular occlusion, either the distal or proximal surface, is contacted with an acidic dissolution fluid for a period of time sufficient for fluid flow to be established through the vascular site. Contact with the vascular site may be accomplished in any convenient manner, so long as it results in the enhancement of fluid flow through the vascular site. Generally, the surface is dynamically contacted or flushed with the acidic dissolution fluid.

By dynamic contact is meant that the fresh dissolution solution is contacted with the surface of the target occlusion one or more times, including continuously, during the treatment period. In many preferred embodiments of the subject methods, the surface of the target occlusion is continuously contacted or flushed with the acidic dissolution fluid. In other words, the acidic dissolution fluid is introduced in a manner such that a continuous flow of the acidic dissolution fluid across the surface of the occlusion is achieved.

Where the surface of the target occlusion is flushed with the dissolution fluid, it is preferred that the pressure in the local environment which includes the surface of the occlusion, i.e. the area bounded by the vessel walls, the surface of the target occlusion and the catheter system used to delivery the solution, remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, where fluid is dynamically contacted with the surface of the target occlusion, fluid is also simultaneously removed from the local environment comprising the surface of the target occlusion, such that the overall volume of fluid in the local environment remains substantially constant, where any difference in volume at any two given times during the treatment period does not exceed about 50%, and usually does not exceed about 10%. As such, the dissolution fluid is introduced into the local environment of the target lesion in a manner such that the local environment remains substantially isovolumetric.

Where the acidic dissolution fluid is dynamically introduced into the vascular site, the dissolution fluid is introduced in a manner such that the flow rate of the dissolution solution through the vascular site of the lesion is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the occlusion, as defined above. The total amount of dissolution fluid that is passed through the local environment of the lesion during the treatment period typically ranges from about 100 to 1000 cc, usually from about 200 to 800 cc and more usually from about 400 to 500 cc. The solution is generally pressurized to achieve the desired flow rate, as described supra. As such, the pressure at the distal end of the coaxial catheter assembly through which the solution is introduced into the local environment typically ranges from about 50 to 1200 psi, usually from about 100 to 600 psi and more usually from about 200 to 400 psi. It is important to note that the overall pressure in the local environment is maintained at substantially isometric or isobaric conditions. As such, the negative pressure at the entrance to the aspiration catheter, e.g. the open annulus at the distal end of the aspiration catheter will be of sufficient magnitude to provide for substantially isobaric conditions. Preferably, the overall pressure in the local environment is maintained at a value ranging from about 0.1 to 3 psi, usually from about 0.5 to 2.5 psi and more usually from about 1 to 2 psi.

Figure 4A:
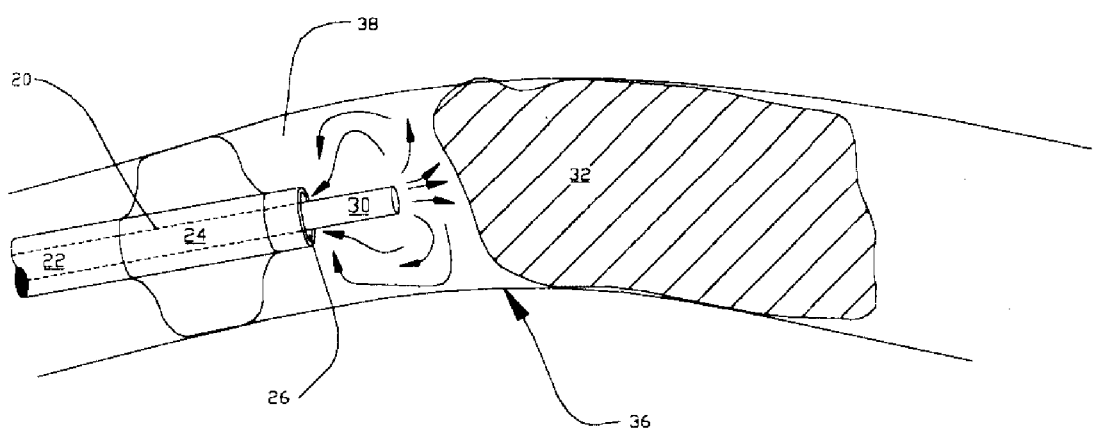
FIG. 4A provides a representation of the use of the coaxial catheter assembly shown in FIG. 2C to flush the surface of a total occlusion; while FIG. 4B provides a representation of the use of the coaxial catheter assembly shown in FIG. 3B to flush the surface of a partial occlusion.
Figure 4B:
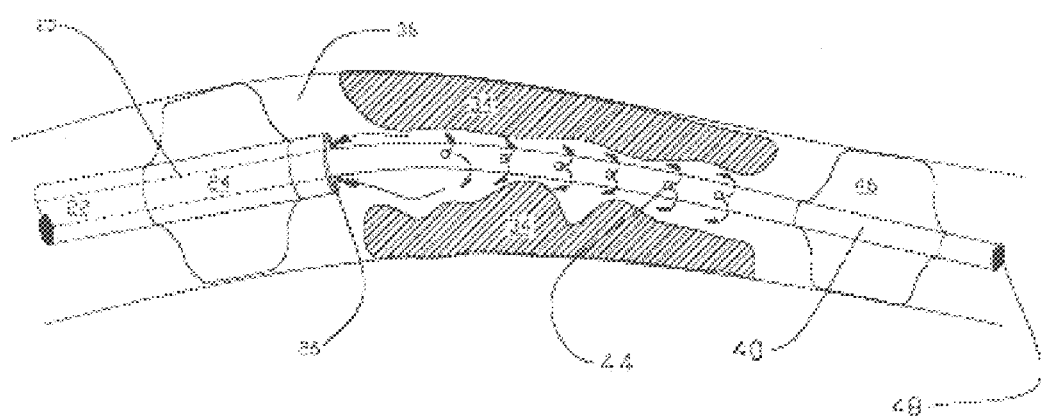

The methods by which the subject catheter systems described above are employed to flush a surface of the target occlusion with the acidic dissolution solution are now further discussed in terms of FIGS. 4A and 4B. FIG. 4A provides a representation of a catheter assembly according to the subject invention flushing a total occlusion in an artery 36. In FIG. 4A, artery 36 is totally occluded by calcified vascular occlusion 32. Coaxial catheter assembly made up of total occlusion catheter insert 30 inside of aspiration catheter 20 is positioned proximal to one surface of occlusion 32, e.g. by advancement over a guidewire with imaging, as described in the experimental section infra. Next, acidic dissolution fluid is introduced through the distal open end of catheter 30, whereby it contacts the proximal surface of the occlusion 32. Simultaneously, fluid is removed from the local environment 38 through the annular space formed at the distal open end 26 of the aspiration catheter 20. The local environment is isolated from the remainder of the host's circulatory system by inflated balloon 24.

FIG. 4B provides a representation of contacting the surface of a partial vascular occlusion using the subject catheter systems. In FIG. 4B, the coaxial catheter assembly that includes partial occlusion catheter insert 46 and aspiration catheter 20 is positioned in the vascular site, e.g. with the aid of a guidewire and imaging, such that the distal end 48 and balloon 46 of the catheter insert are on one side of partial occlusion 34 and the distal end 26 and balloon 24 of aspiration catheter 20 are on the other side of partial occlusion 34. Fluid is then introduced into the local environment (i.e. the space bordered by the arterial walls and the two balloons) through infusion ports 44. Simultaneously, fluid is removed through the annular space present at the distal end 26 of aspiration catheter 20, as indicated by the arrows.

Time Period

The surface of the target occlusion is contacted, e.g. flushed, with the acidic dissolution fluid for a period of time sufficient for fluid flow to be enhanced through the vascular site, e.g. established or improved. As such, where the target occlusion is a total occlusion, contact is maintained for a period of time sufficient for a guidewire to be passed through the vascular site, as described above. Alternatively, where the target occlusion is a partial occlusion, contact is achieved for a period of time sufficient for the rate of fluid flow to be increased through the vascular site, generally by at least about 10%, usually by at least about 50%, and in many embodiments by at least about 100%. Generally, the period of time during which the surface of the occlusion is contacted with the acidic dissolution solution ranges from about 5 to 100 minutes, usually from about 10 to 30 minutes. Where contact is achieved by flushing the target occlusion with the acidic dissolution solution, the contact duration typically lasts for a period of time ranging from about 5 to 30 minutes, usually from about 10 to 30 minutes and more usually from about 10 to 20 minutes.

Acidic Dissolution Solutions

A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of a red blood cell, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Hydrogen Chloride Solutions

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

Further Embodiments of the Subject Methods

In a number of embodiments of the subject methods, the methods in which the surface of the target occlusion is contacted with an acidic dissolution fluid may be modified to include a number of additional method steps. Additional method steps that may be present in the overall process include: rendering the local environment of the target occlusion bloodless, contacting the target occlusion with a solution designed to remove organic components, washing or rinsing the local environment of the target occlusion, applying external energy to the target occlusion; imaging the target vascular site; establishing or expanding a passageway through an initial thrombotic domain of the target occlusion; and the like.

Rendering the Local Environment Bloodless

In many preferred embodiments, as described above, the local environment of the target occlusion is rendered substantially bloodless prior to introduction of the dissolution fluid. In these embodiments, the balloon(s) of the assembled catheter system is inflated to physically isolated the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution includes an anticlotting factor in many embodiments, where anticlotting factors of interest include heparin and the like. The washing solution can also contain chelating agents.

Use of Organic Structure Dissolution Solutions

As mentioned above, in addition to the acidic dissolution solution, certain embodiments of the subject invention include a step of contacting the target occlusion with a dissolution solution which serves to remove at least a portion of the non-mineral, typically organic, phase of the target occlusion. The nature of this "organic phase dissolution solution" varies depending on the nature of the target occlusion. Representative active agents that may be present in this organic phase dissolution solution include: oxidizing agents; organic solvents; lipid dissolving agents such as surfactants, e.g. TWEEN™, and detergents, where ionic detergents are of particular interest, e.g. cholic acid, glycocholic acid, benzylkonium chloride; enzymes, and the like.

Application of External Energy

In certain embodiments, external energy is applied to the vascular site to promote mechanical break-up of the occlusion into particles or debris that can be easily removed from the vascular site. Any means of applying external energy to the vascular site may be employed. As such, jets or other such means on a catheter device which are capable of providing varying external forces to the occlusion sufficient to cause the occlusion to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the target occlusion. There are several devices for the application of ultrasound to cardiovascular tissue known to those of skill in the art. See e.g. U.S. Pat. Nos. 4,808,153 and 5,432,663, the disclosures of which are herein incorporated by reference.

In such methods where external energy is applied to the occlusion in order to disrupt or break-up the occlusion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the vascular site. Particles may be removed from the vascular site using any convenient means, such as the catheter of the subject invention described in greater detail infra.

Another means that may be employed to apply external energy to the lesion during the dissolution process is to use a mechanical means of applying external energy. Mechanical means of interest include moving structures, e.g. rotating wires, guidewires, which physically contact the target occlusion and thereby apply physical external energy to the target lesion.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography; rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Thrombus Removal Step

The subject methods may further include a thrombus removal step, e.g. where the calcified domain of the target occlusion is covered by a thrombotic domain, as described above. In such methods, any thrombus removal means that is capable of providing sufficient access of the acidic dissolution solution to the surface the calcified domain of the target lesion may be employed. Thus, where the thrombotic domain is a disorganized domain, it may be sufficient to pass increasingly larger diameter guidewires through the domain until a passageway of sufficient width to provide access of the catheter assembly described above to the surface of the occlusion is established. Alternatively, portions of the thrombotic domain may be removed, e.g. via atherectomy methods, angioplasty methods, and the like, where devices for performing such procedures are known to those of skill in the art. See the patent references cited in the Relevant Literature section, supra, which references are herein incorporated by reference.

Use of a Plurality of Solutions

In many embodiments, the subject methods include contacting the surface of the target occlusion with a plurality, i.e. two or more, distinct solutions, one of which is an acidic dissolution solution. Where one or more additional distinct solutions, such as priming solutions, washing solutions, organic phase dissolution solutions and the like are employed, as described below, such disparate solutions are generally introduced sequentially to the vascular site. For example, the target occlusion may be contacted with the following order of solutions: (1) washing solution to render the local environment substantially bloodless; (2) organic phase dissolution solution, e.g. detergent solution such as cholic acid solution, to remove organic phases from the target lesion; (3) acidic dissolution solution to demineralize the target occlusion; and (4) washing solution. Other sequences of solution application can also be employed. See U.S. patent application Ser. No. 09/353,127, the disclosure of which is herein incorporated by reference.

Outcome

As discussed above, the subject methods result in the enhancement of fluid flow through the vascular site occupied by the occlusion. Fluid flow is considered to be enhanced in those situations where the vascular site is totally occluded when a guide wire can be moved through the vascular site without significant resistance. Fluid flow is considered to be enhanced in those situations in which the vascular site is partially occluded when the rate of fluid flow through the vascular site increases by at least 10%, usually by at least 50% and in many embodiments by at least 100%.

In certain embodiments, the subject methods will not result in complete removal of the target occlusion from the vascular site. As such, the vascular site, while not totally occluded, may still include lesion deposits on the wall which impede fluid flow through the vascular site and the removal or reduction of which is desired. Any convenient protocol for treating these remaining deposits may be employed, e.g. balloon angioplasty, atherectomy, stenting, etc. Also of interest is the use of two balloon catheters and an acidic dissolution solution, as described in PCT/US99/15918, the disclosure of which is herein incorporated by reference.

Of particular interest in those embodiments where the vascular site is initially totally occluded, fluid flow through the total occlusion is first established using the catheter assembly made up of the total occlusion catheter insert inside the aspiration catheter. Following establishment of fluid flow, the rate of fluid flow is increased using the catheter assembly made up of the partial occlusion catheter insert inside the aspiration catheter.

Systems

Also provided by the subject invention are systems for practicing the subject methods, i.e. for enhancing fluid flow through a vascular site occupied by a vascular occlusion. The subject systems at least include the catheter systems as described above, a manifold, a fluid reservoir for storing acidic dissolution fluid and a negative pressure means for providing aspiration or suction during use of the system. The systems may further include a number of optional components, e.g. guidewires, pumps for pressurizing the dissolution fluid, and the like.

Figure 5A:
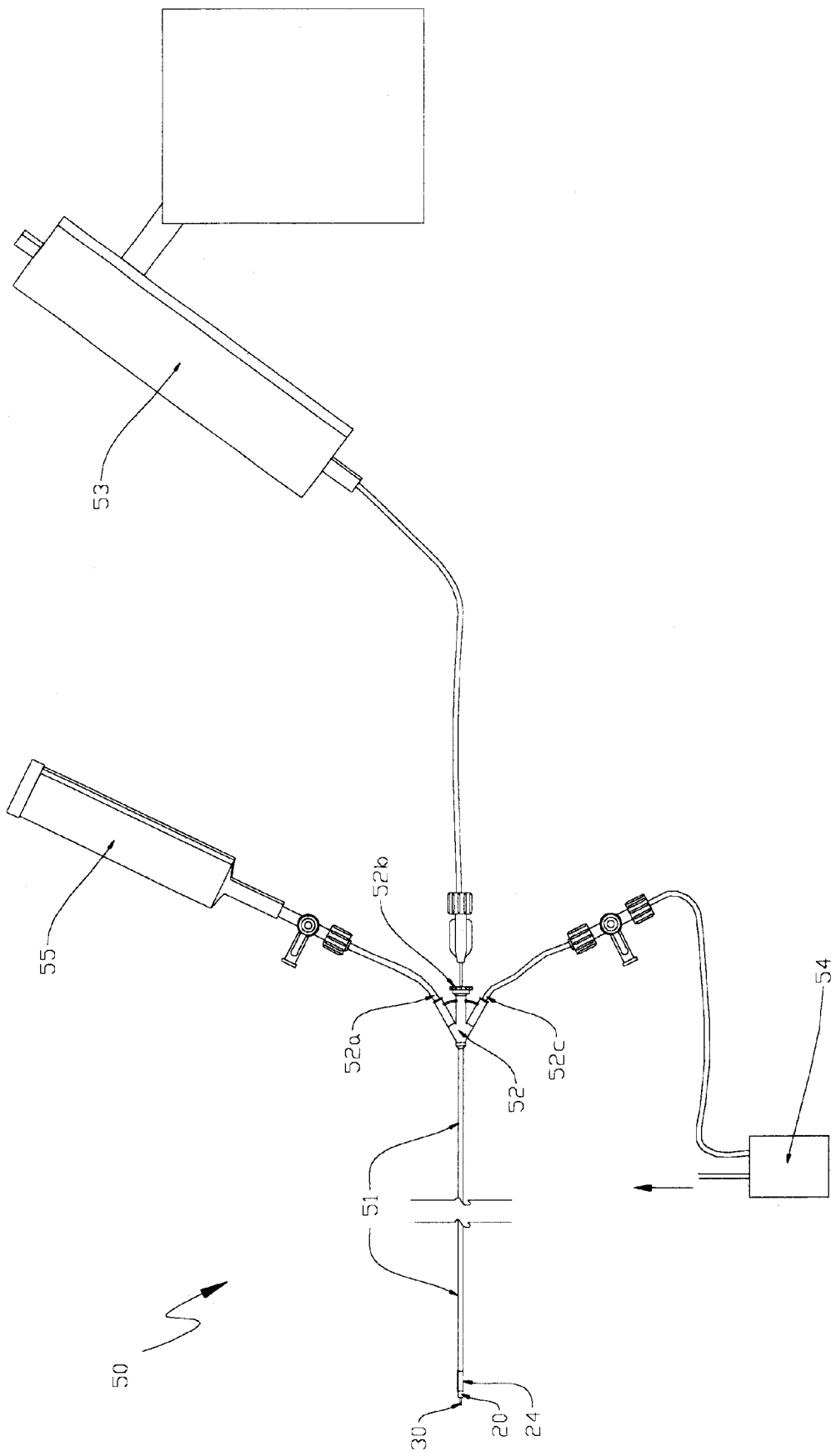
FIGS. 5A and 5B provide diagrams of systems comprising the coaxial catheter assembly of FIG. 2C and FIG. 3B, respectively.

In the system depicted in FIG. 5A, system 50 includes catheter assembly 51, manifold 52 with three entry ports (52a, 52b and 52c), acidic dissolution fluid reservoir 53, negative pressure means 54 and balloon inflation means 55. Catheter assembly 51 is as described in FIG. 2C, having aspiration catheter 20 encompassing total occlusion catheter insert 30. Balloon 24 is positioned on the aspiration catheter at a location proximal to the distal end of the aspiration catheter. Manifold 52 has three ports, 52a, 52b and 52c. Port 52a serves as the balloon port, and is attached to a balloon inflation means 55, e.g. a syringe, during use. The syringe 55 is in fluid or gaseous communication with the interior of balloon 24 through a lumen that extends the length of the aspiration catheter (not shown). Port 52b serves as the guidewire port and injection port, and is attached in fluid communication to acidic dissolution fluid reservoir 53 during use. In certain embodiments, a pumping means (not shown) may be present to provide for desired pressure of the acidic dissolution fluid into the fluid introduction means and out of the distal end of the catheter device 51. Port 52c serves as the aspiration port through which fluid travels from the vascular site through the catheter device 51 and out of the patient. Port 52c is connected to negative pressure means 54 and optionally fluid outflow reservoir (not shown).

Figure 5B:
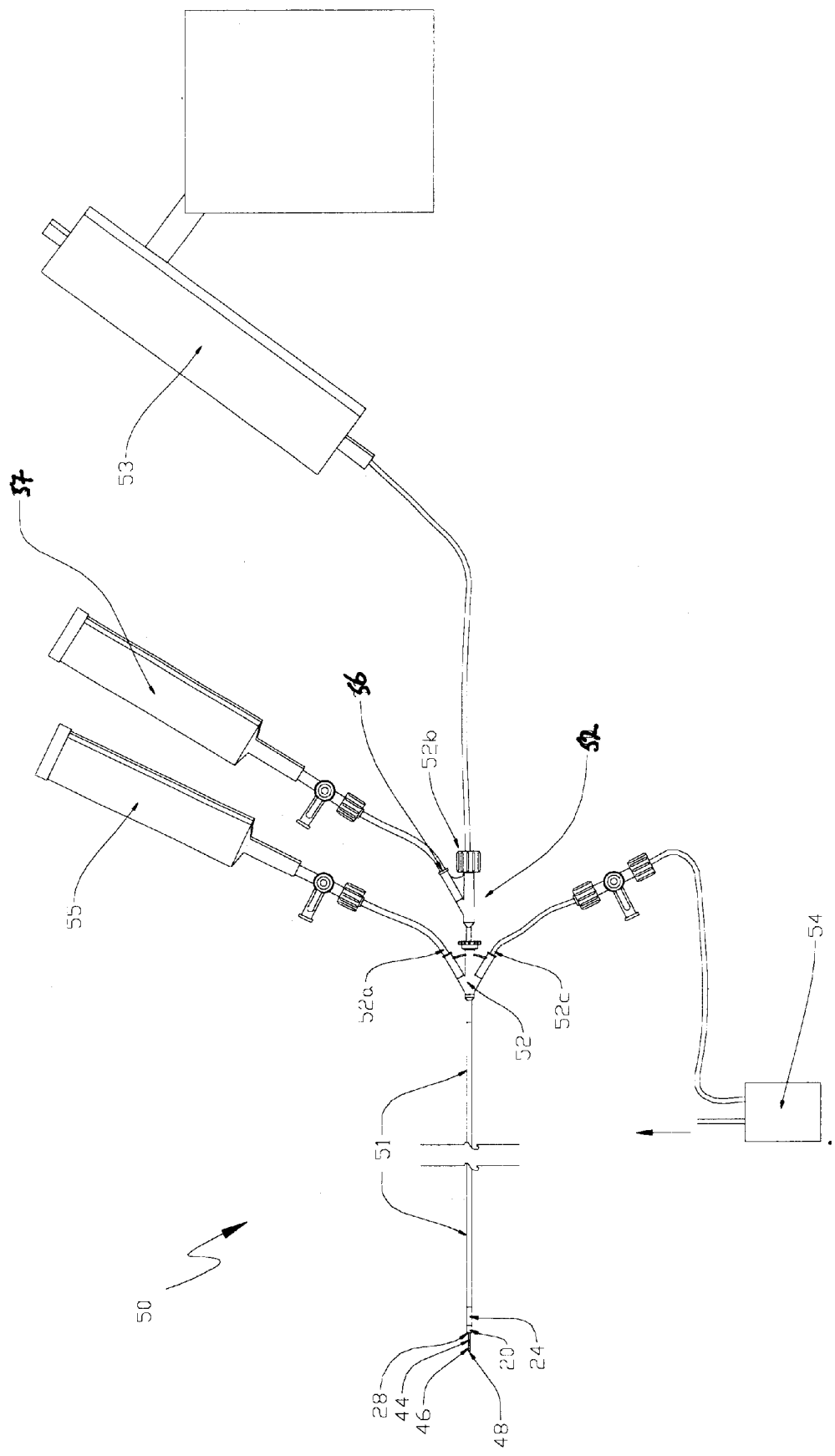

The system shown in FIG. 5A is one which is ready for use in the treatment of a total vascular occlusion, as described above. In those embodiments where one wishes to treat a partial vascular occlusion using a catheter assembly having a partial occlusion catheter insert inside an aspiration catheter, as shown in FIGS. 3B and 4B, an analogous system as depicted in FIG. 5B is employed. The system depicted in FIG. 5B is analogous to that shown in FIG. 5A. In the assembly shown if FIG. 5B, manifold 52 in an expanded manifold that includes additional port 56 for second balloon inflation means 57.

Utility

The subject devices and methods find use in a variety of different applications in which it is desired to enhance fluid flow, usually blood flow, (or at least pass a guidewire through), a vascular site that is occupied by a calcified vascular occlusion, e.g. a partial or total occlusion. As such, the subject methods and devices find use in the treatment of peripheral vascular disease, etc. The subject methods also find use in the treatment of coronary vascular diseases. By treatment is meant that a guidewire can at least be passed through the vascular site under conditions which, prior to treatment, it could not. Treatment also includes situations where the subject methods provide for larger fluid passageways through the vascular site, including those situations where fluid flow is returned to substantially the normal rate through the vascular site. The subject methods may be used in conjunction with other methods, including balloon angioplasty, atherectomy, and the like, as part of a total treatment protocol.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Kits

Also provided by the subject invention are kits for use in enhancing fluid flow through a vascular site occupied by an occlusion. The subject kits at least include a catheter system, as described above, where the catheter system at least includes an spiration catheter and one of, usually both of, a partial occlusion catheter insert and a total occlusion catheter insert. The kits may further include one or more additional components and accessories for use with the subject catheter systems, including tubing for connecting the various catheter components with fluid reservoirs, syringes, pumping means, etc., connectors, one or more guidewires, dilators, vacuum regulators, etc.

In certain embodiments, the kits further include one or more solutions, or precursors thereof, where. in such embodiments the kits at least include an acidic dissolution fluid, such as a hydrochloric acid solution, as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 1 to 500 liters, usually from about 10 to 200 liters and more usually from about 50 to 100 liters. Alternatively, the kit may comprise precursors of the dissolution solution for use in preparing the solution at the time of use. For example, the precursors may be provided in dry form for mixing with a fluid, e.g. water, at the time of use. In addition to the dissolution fluid or precursors thereof, the kit may further comprise one or more additional fluids (or dry precursors thereof), such as a priming solution, a washing solution, contrast medium, and the like.

Other elements that may be present in the subject kits include various components of the systems, including manifolds, balloon inflation means, e.g. syringes, pumping means, negative pressure means etc.

Finally, the kits will include instructions for practicing the subject methods, where such instructions may be present on one or more of the kit components, the kit packaging and/or a kit package insert.

The following examples are offered by way of illustration and not by way of limitation.

Experimental

I. A 50 year old male having a total occlusion in the superficial femoral artery (SFA) as shown in FIG. 1 is treated as follows. In FIG. 1, the external iliac artery is shown as it branches into the SFA 12 and the profunda 13. Also shown are the medial circumflex and the later circumflex, 14 and 15 respectively. The SFA is totally occluded by occlusion 16.

Figure 6:
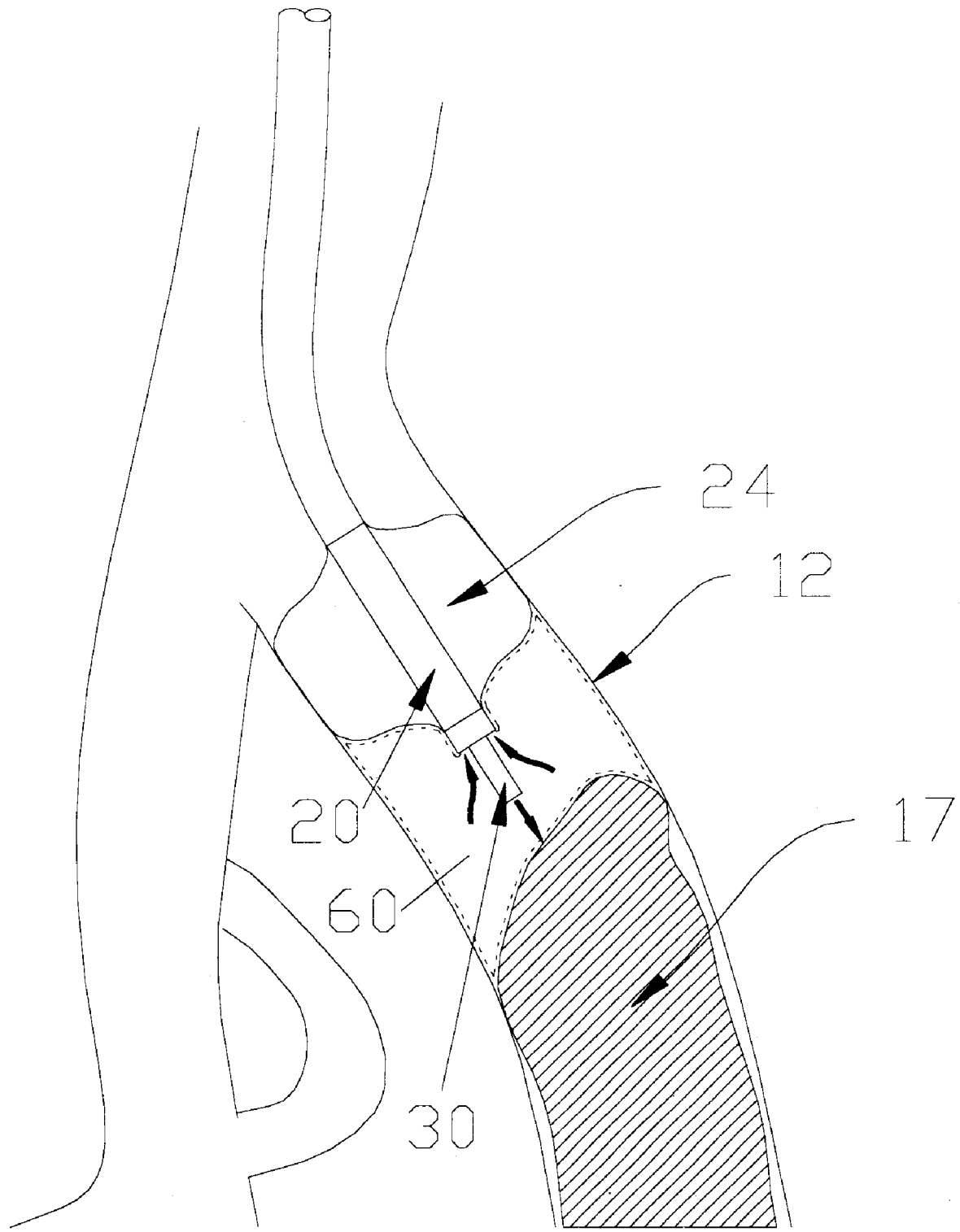
FIGS. 6 to 8 provide a sequential representation of the occluded vessel shown in FIG. 1 being treated according to the subject invention.
Figure 7:
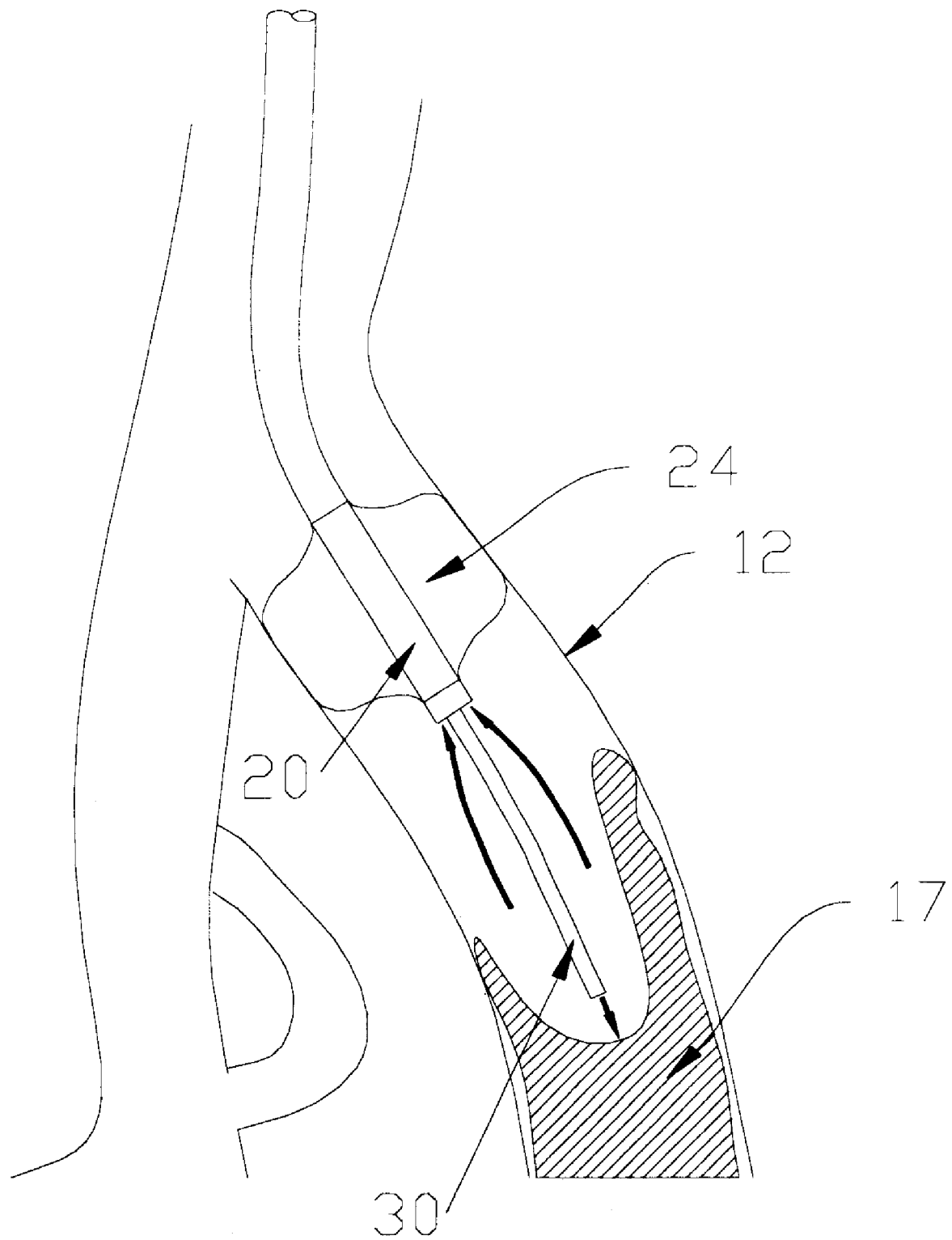
Figure 8:
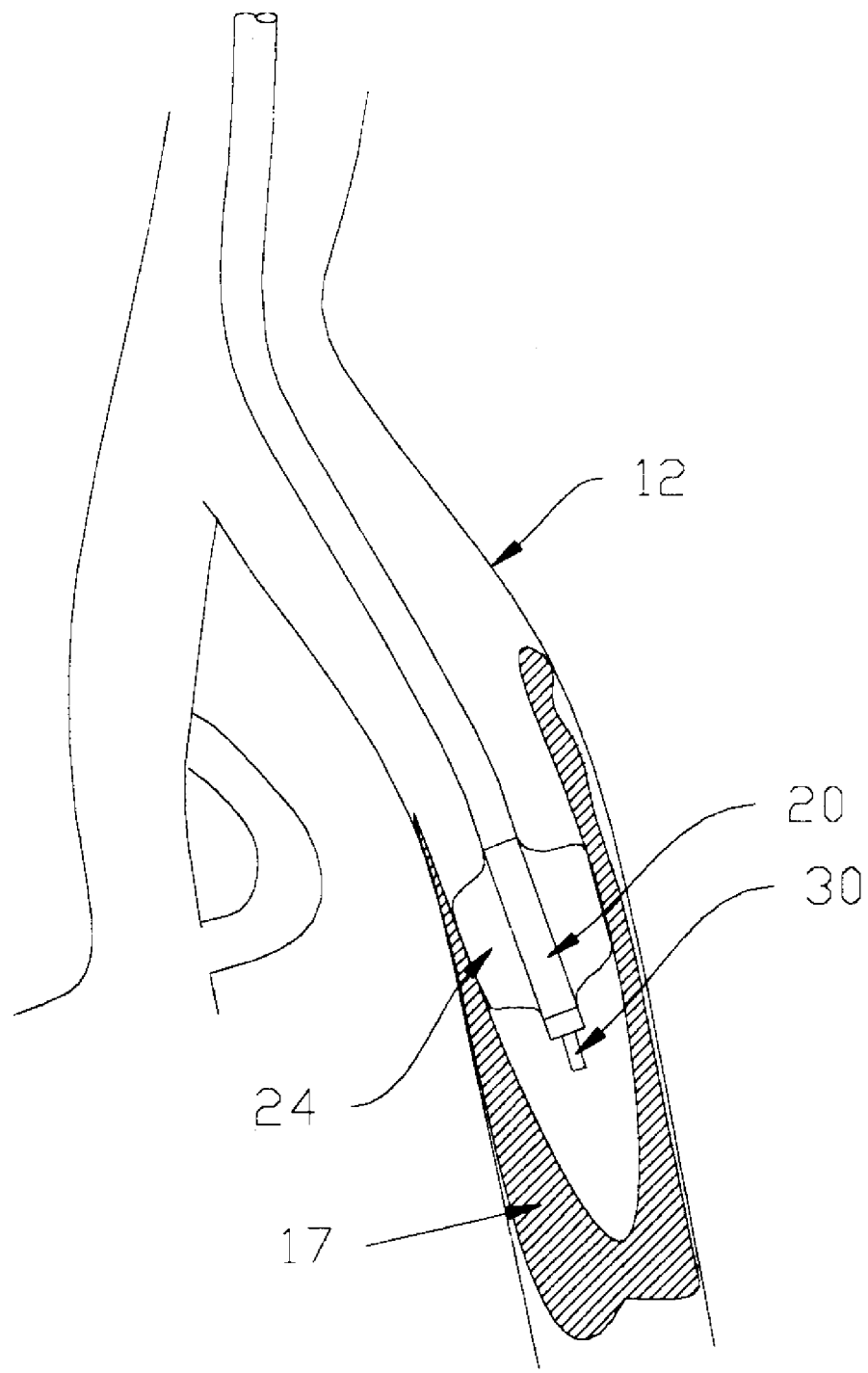

1. The patient is heparinized using standard procedures.
2. An introducer sheath is placed either in the same leg to provide retrograde access or in the opposite leg to provide cross-over access.
3. A guidewire is inserted and advanced to the site of the total occlusion.
4. The catheter system as shown in FIG. 5A is employed as follows. The catheter device is inserted so that the distal end of the device is at the vascular site occupied by the total occlusion, as shown in FIG. 6. The balloon 24 is then inflated by depressing the syringe 55, such that the balloon occludes the vessel proximal to the occlusion, as shown in FIG. 6. The local environment 60 bordered by the proximal surface of the occlusion, the SFA vessel walls and the distal surface of the inflated balloon 24 is indicated by dashed lines.
5. Contrast medium is then injected into the vascular site through port 52b to confirm the location of the distal end of the catheter and the inflated balloon.
6. A sufficient amount of heparinized phosphate buffered saline is then injected through port 52b into the isolated vascular site or local environment 60 and aspirated therefrom such that the isolated local environment 60 is rendered substantially bloodless.
7. The surface of the total occlusion is then flushed with acidic dissolution fluid A (0.1N HCl, 0.05 M NaCl) by introducing solution A through port 52b into the vascular space and removing or aspirating fluid from the vascular site through port 52c, as shown in FIG. 6. See also FIG. 4A.
8. As the occlusion is demineralized, the central fluid introduction catheter 30 is advanced independent of the aspiration catheter/outer catheter 20, as shown in FIG. 7.
9. Where desired, balloon 24 may be deflated, aspiration catheter 20 repositioned, and then balloon 24 may be reinflated to move the distal end of the total occlusion catheter insert 30 to a site further into the occlusion 17, as shown in FIG. 8.
10. Once a passage through the occlusion sufficient to pass a guidewire through the occlusion is produced, the device is removed.
11. The above procedure results in fluid flow through the vascular site occupied by the lesion being reestablished, as evidenced by passing a guidewire through the vascular site.
12. Where desired, following reestablishment of fluid flow through the total occlusion, the total occlusion catheter insert is removed. A guidewire is then inserted through the large lumen of aspiration catheter 20 to a space beyond the distal end of the occlusion. A partial occlusion catheter insert is then introduced over the guidewire to a position such that the balloon at the distal end of the insert is on the far side of the partial occlusion.
13. A system as shown in FIG. 5B is then employed to inflate the balloon of the insert, establish a bloodless local environment and flush the remaining partial occlusion with acidic dissolution fluid, as shown in FIG. 4B.

II. Variations on the Above Procedure

Figure 9:
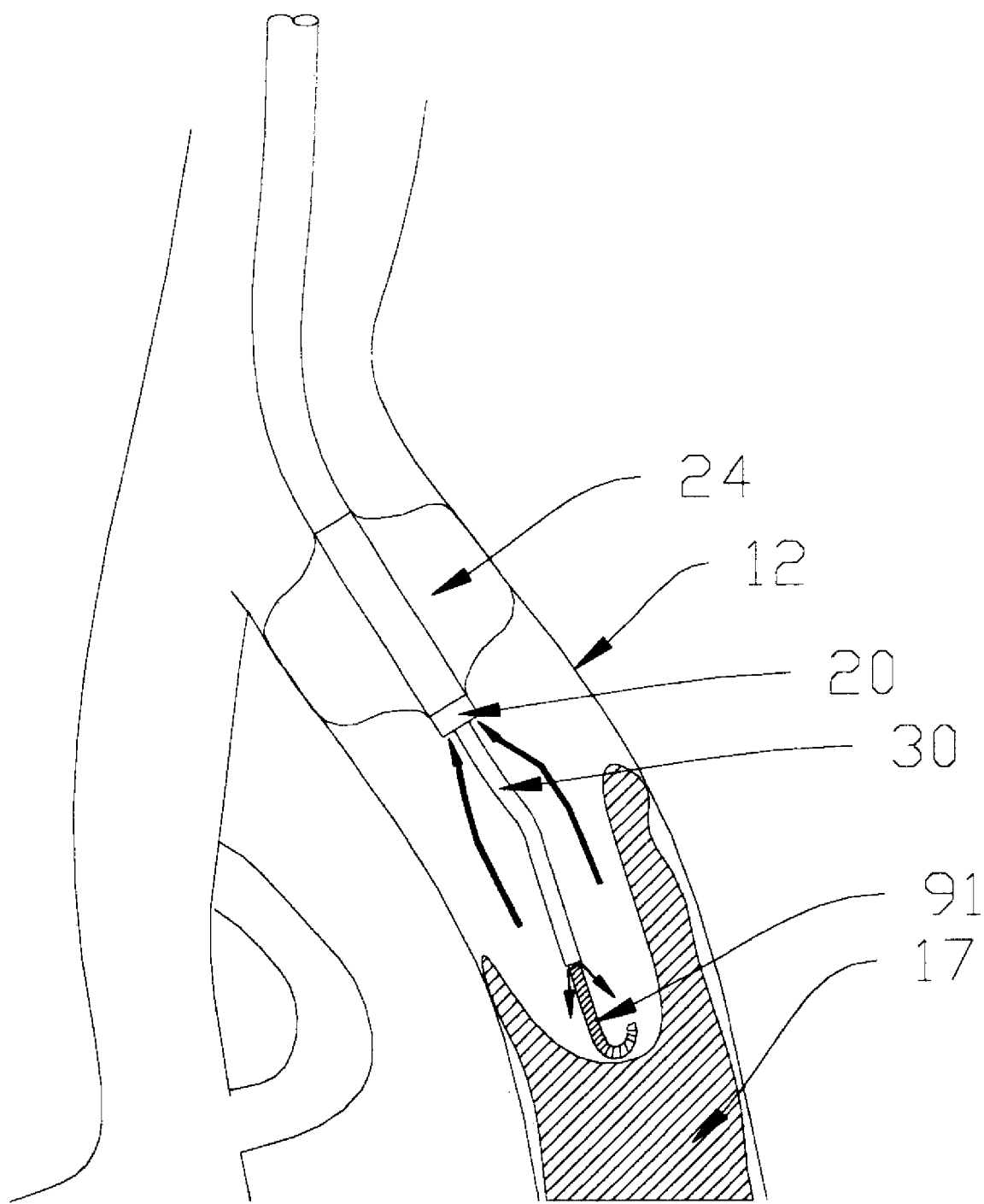
FIGS. 9 and 10 provide views of alternative embodiments of the subject methods in which external energy is applied to the occlusion, e.g. by movement of a guidewire as shown in FIG. 9.
Figure 10:
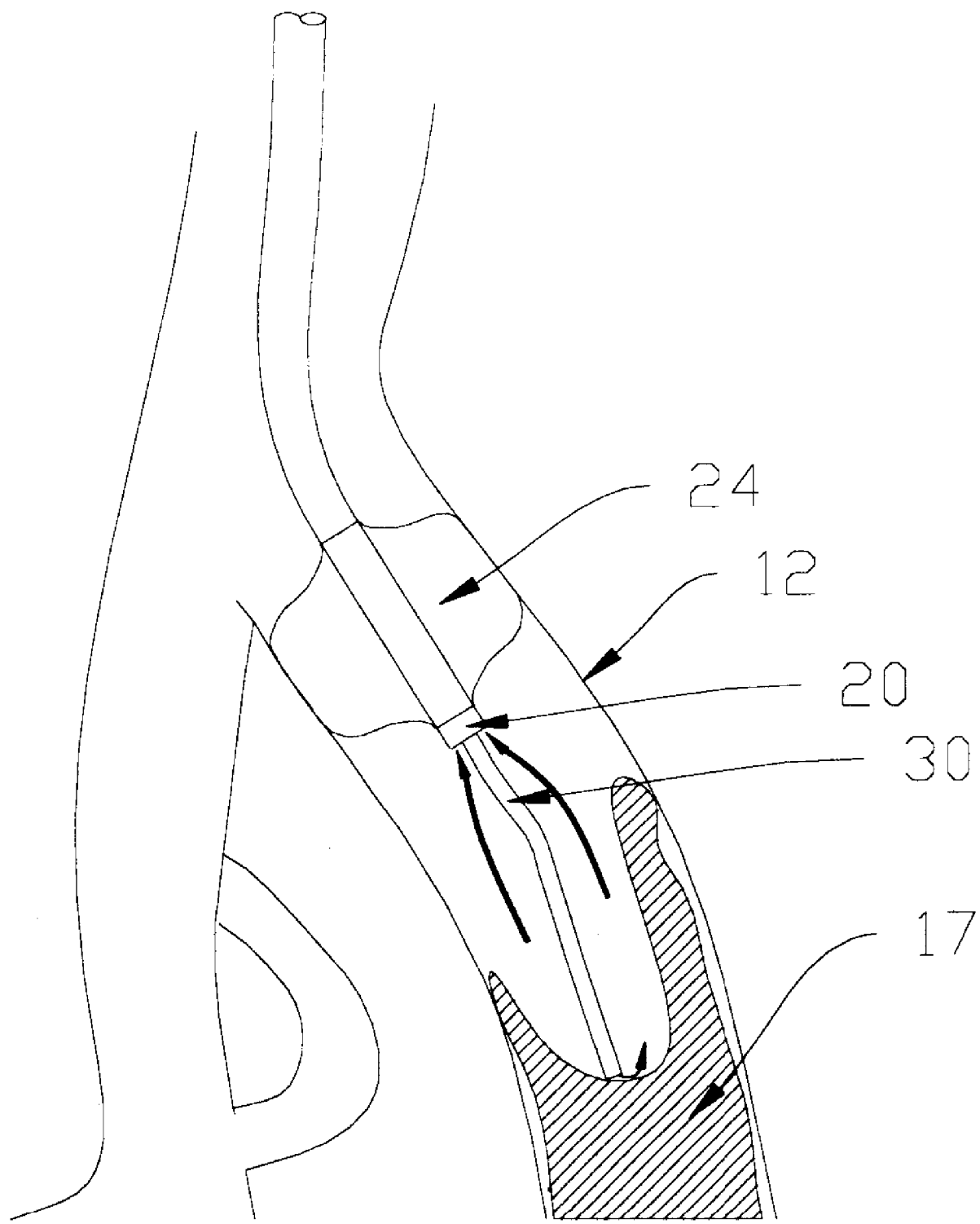

The above procedure is performed with the additional step of applying mechanical energy to the occlusion during flushing with the acidic dissolution solution. FIG. 9 shows mechanical energy being applied to the occlusion by contacting a guidewire 91 with the surface of the total occlusion during flushing. FIG. 10 shows mechanical energy being applied to the surface of the occlusion with the proximal end of the total occlusion insert. Other means of applying external energy, e.g. mechanical energy, may also be employed.

It is evident from the above discussion and results that improved methods of enhancing blood flow through a vascular occlusion are provided. Specifically, the subject invention provides a means for readily establishing fluid flow through a vascular site totally occluded by a calcified vascular occlusion, which has heretofore been difficult to practice. As such, the subject invention provides a means for using less traumatic procedures for treating peripheral vascular disease, thereby delaying or removing the need for graft procedures and/or amputation. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An aqueous acidic dissolution fluid consisting essentially of:

hydrogen chloride in a concentration ranging from about 0.01 to 1.0 N; and a salt in a concentration ranging from 0.05 to 0.25 M.

2. The solution according to claim 1, wherein said salt is NaCl.

3. The solution according to claim 2, wherein said NaCl is present in a concentration ranging from about 0.05 to 0.1 M.

4. An aqueous acidic dissolution fluid consisting essentially of:

hydrogen chloride in a concentration ranging from about 0.01 to 1.0 N; and

NaCl in a concentration ranging from 0.05 to 0.25 M.

5. The solution according to claim 4, wherein said hydrogen chloride is present in a concentration ranging from about 0.05 to 0.5N.

6. The solution according to claim 5, wherein said hydrogen chloride is present in an amount ranging from about 0.075 to about 0.25 N.

7. The solution according to claim 4, wherein said NaCl is present in an amount ranging from 0.05 to 0.10 M.

8. An aqueous acidic dissolution fluid consisting essentially of:

hydrogen chloride in a concentration ranging from about 0.05 to 0.5N; and

NaCl in a concentration ranging from 0.05 to 0.10 M.

9. An aqueous acidic dissolution fluid consisting essentially of:

hydrogen chloride in a concentration ranging from about 0.075 to about 0.25 N; and NaCl in a concentration ranging from.0.05 to 0.10 M.

10. A kit for use in enhancing fluid flow through a vascular site occupied by a vascular occlusion, said kit comprising:
   (a) an aqueous acidic dissolution fluid consisting essentially of:
      (i) hydrogen chloride in a concentration ranging from about 0.01 to 1.0N; and
      (ii) a salt in a concentration ranging from 0.05 to 0.25 M; and
   (b) instructions for using said aqueous acidic dissolution fluid to enhance fluid flow through a vascular site occupied by a vascular occlusion.

11. The kit according to claim 10, wherein said salt is NaCl.

12. The kit according to claim 11, wherein said NaCl is present in a concentration ranging from 0.05 to 0.1 M.

13. A kit for use in enhancing fluid flow through a vascular site occupied by a vascular occlusion, said kit comprising:
   (a) an aqueous acidic dissolution fluid consisting essentially of:
      (i) hydrogen chloride in a concentration ranging from about 0.01 to 1.0N; and
      (ii) NaCl in a concentration ranging from 0.05 to 0.25 M; and
   (b) instructions for using said aqueous acidic dissolution fluid to enhance fluid flow through a vascular site occupied by a vascular occlusion.

14. The kit according to claim 13, wherein said hydrogen chloride is present in a concentration ranging from about 0.05 to 0.5N.

15. The kit according to claim 14, wherein said hydrogen chloride is present in an amount ranging from about 0.075 to about 0.25 N.

16. The kit according to claim 13, wherein said NaCl is present in an amount ranging from 0.05 to 0.10 M.

17. A kit for use in enhancing fluid flow through a vascular site occupied by a vascular occlusion, said kit comprising:
   (a) an aqueous acidic dissolution fluid consisting essentially of:
      (i) hydrogen chloride in a concentration ranging from about 0.01 to 1.0N; and
      (ii) a salt in a concentration ranging from 0.05 to 0.25 M;
   (b) a catheter; and
   (c) instructions for using said aqueous acidic dissolution fluid to enhance fluid flow through a vascular site occupied by a vascular occlusion.

18. The kit according to claim 17, wherein said salt is NaCl.

* * * * *

UNITED STATES PATENT AND TRADEMARK OFFICE
CERTIFICATE OF CORRECTION

PATENT NO.    : 6,527,979 B2
DATED         : March 4, 2003
INVENTOR(S)   : Constantz, Brent R.

It is certified that error appears in the above-identified patent and that said Letters Patent is hereby corrected as shown below:

Column 7,
Line 19, insert -- Z -- following "and" and before "is"

Column 14,
Line 37, change "spiration" to -- aspiration --
Line 46, delete "." following "where"

Signed and Sealed this

Fifth Day of August, 2003

JAMES E. ROGAN
*Director of the United States Patent and Trademark Office*